United States Patent
Simonnet et al.

(12)

(10) Patent No.: US 6,464,990 B2
(45) Date of Patent: *Oct. 15, 2002

(54) NANOEMULSION BASED ON ETHYLENE OXIDE AND PROPYLENE OXIDE BLOCK COPOLYMERS AND ITS USES IN THE COSMETICS, DERMATOLOGICAL AND/OR OPHTHALMOLOGICAL FIELDS

(75) Inventors: Jean-Thierry Simonnet; Odile Sonneville, both of Paris; Sylvie Legret, Chatillon, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/477,715

(22) Filed: Jan. 5, 2000

(65) Prior Publication Data

US 2002/0015721 A1 Feb. 7, 2002

(30) Foreign Application Priority Data

Jan. 5, 1999 (FR) ............................................. 99 00031

(51) Int. Cl.$^7$ ............................. A61K 6/00; A61K 7/00; A61K 31/74
(52) U.S. Cl. .................... 424/401; 424/400; 424/78.03; 424/450; 514/873; 514/937; 514/938
(58) Field of Search ................................ 424/59, 70.23, 424/70.19, 78.03, 193.1, 400, 401, 402, 450, 427; 514/2, 785, 788, 937; 516/57, 72; 138/118.1

(56) References Cited

U.S. PATENT DOCUMENTS

| 4,486,405 | A | * | 12/1984 | Klein | 424/59 |
| 4,954,338 | A | * | 9/1990 | Mattox | 424/78 |
| 4,960,814 | A | * | 10/1990 | Wu et al. | 524/312 |
| 5,098,606 | A | * | 3/1992 | Nakajimia et al. | 252/358 |
| 5,216,033 | A | * | 6/1993 | Pereira et al. | 514/844 |
| 5,747,009 | A | * | 5/1998 | Hansenne | 424/59 |
| 5,753,241 | A | * | 5/1998 | Ribier et al. | 424/401 |
| 5,861,148 | A | * | 1/1999 | Smith | 424/78.04 |
| 5,997,851 | A | * | 12/1999 | Cox et al. | 424/70.1 |
| 6,051,211 | A | * | 4/2000 | Hansenne et al. | 424/59 |

FOREIGN PATENT DOCUMENTS

| EP | 0 842 652 | 5/1998 |
| EP | 0 852 941 | 7/1998 |

* cited by examiner

*Primary Examiner*—Thurman K. Page
*Assistant Examiner*—Charesse Evans
(74) *Attorney, Agent, or Firm*—Oblon, Spivak, McClelland, Maier & Neustadt, P.C.

(57) ABSTRACT

A nanoemulsion comprising an oily phase dispersed in an aqueous phase and having oil globules with a number-average size of less than 100 mm, which dispersion is facilitated by a surfactant comprised of polyethylene oxide and polypropylene oxide blocks, the oily phase comprising at least one oil having a molecular weight of greater than 400 and wherein the ratio by weight of the amount of oily phase to the amount of surfactant ranges from 2 to 10.

26 Claims, No Drawings

NANOEMULSION BASED ON ETHYLENE OXIDE AND PROPYLENE OXIDE BLOCK COPOLYMERS AND ITS USES IN THE COSMETICS, DERMATOLOGICAL AND/OR OPHTHALMOLOGICAL FIELDS

BACKGROUND OF THE INVENTION

1. Field of the Invention

The present invention relates to a nanoemulsion based on a surfactant having polyethylene oxide and polypropylene oxide blocks and on at least one oil having a molecular weight of greater than 400, the ratio by weight of the amount of oily phase to the amount of surfactant ranging from 2 to 10. The present invention also relates to a process for the preparation of the nanoemulsion and to its uses in the cosmetics, dermatological and/or ophthalmological fields. This nanoemulsion is stable on storage and can comprise large amounts of oil while retaining good transparency and while having good cosmetic properties.

2. Description of the Background

Nanoemulsions are oil-in-water emulsions, the oil globules of which have a very fine particle size, that is to say a number-average size of less than 100 nm. They are generally manufactured by mechanical fragmentation of an oily phase in an aqueous phase in the presence of a surfactant. In the case of nanoemulsions, the very small size of the oily globules is obtained in particular by virtue of at least one pass through a high-pressure homogenizer. The small size of the globules confers on them cosmetically advantageous properties which distinguish them from conventional emulsions: they are transparent and exhibit a uniquely different texture. They can also carry active principles more efficiently.

Transparent microemulsions are known in the art. In contrast to nanoemulsions, microemulsions are not, strictly speaking, emulsions; they are transparent solutions of micelles swollen by oil, which oil is generally a very-short-chain oil such as hexane or decane, and is solubilized by virtue of the joint presence of a significant amount of surfactants and of cosurfactants which form the micelles. The size of the swollen micelles is very small because of the small amount of oil which they can solubilize. This very small size of the micelles is the cause of their transparency, as with nanoemulsions. However, in contrast to nanoemulsions, microemulsions are spontaneously formed by mixing the constituents, without contributing mechanical energy other than simple magnetic stirring. The major disadvantages of microemulsions are related to their high proportion of surfactants, leading to intolerance and resulting in a sticky feel during application to the skin. Furthermore, their formulation range is generally very narrow and their temperature stability very limited.

In addition, nanoemulsions are known in the art which comprise an amphiphilic lipid phase composed of phospholipids, water and oil. These emulsions exhibit the disadvantage of being unstable on storage at conventional storage temperatures, i.e., from 0 to 45° C. They lead to yellow compositions and produce rancid smells which develop after several days of storage.

Nanoemulsions stabilized by a lamellar liquid crystal coating, obtained by the combination of a hydrophilic surfactant and of a lipophilic surfactant, are also known. However, these combinations are problematic to prepare. Furthermore, the nanoemulsions obtained exhibit a waxy and film-forming feel which is not very pleasant for the user.

Furthermore, EP 0 728 460 discloses nanoemulsions which are based on fluid non-ionic amphiphilic lipids. However, these nanoemulsions exhibit the disadvantage of having a sticky effect during application to the skin. A need, therefore, continues to exist for nanoemulsions which have neither the disadvantages of those of the prior art nor the disadvantages of microemulsions.

SUMMARY OF THE INVENTION

Accordingly, one object of the present invention is to provide a nonoemulsion which exhibits all of the advantages of known nanoemulsions without their disadvantages.

Briefly, this object and other objects of the present invention as hereinafter will become more readily apparent can be attained by a nanoemulsion comprising an oily phase dispersed in an aqueous phase and having oil globules with a number-average size of less than 100 nm, which dispersion is facilitated by a surfactant comprised of polyethylene oxide and polypropylene oxide blocks, the oily phase comprising at least one oil having a molecular weight of greater than 400 and wherein the ratio by weight of the amount of oily phase to the amount of surfactant ranges from 2 to 10.

DETAILED DESCRIPTION OF THE PREFERRED EMBODIMENTS

The nanoemulsions of the invention generally have a transparent to bluish appearance. Their transparency is measured by a transmittance coefficient at 600 nm ranging from 10 to 90% or else by a turbidity ranging from 60 to 600 NTU, preferably from 70 to 300 NTU, which turbidity is measured with a Hach Model 2100 P portable turbidimeter.

The oil globules of the nanoemulsions of the invention have a number-average size of less than 100 nm, preferably ranging from 20 to 75 nm, more preferably from 40 to 60 nm. The decrease in the size of the globules makes it possible to promote the penetration of the active principles into the surface layers of the skin (carrier effect).

The surfactant which can be used in the nanoemulsion of the invention is selected from ethylene oxide and propylene oxide block copolymers, and their mixtures, and, preferably, the nanoemulsion of the invention is devoid of any surfactant other than ethylene oxide and propylene oxide block copolymers.

The ethylene oxide and propylene oxide block copolymers which can be used as surfactant in the nanoemulsion of the invention can be selected, in particular, from the block copolymers of formula (I):

$$HO(C_2H_4O)_x(C_3H_6O)_y(C_2H_4O)_zH \quad\quad (I)$$

wherein x, y and z are integers such that x+z ranges from 2 to 100 and y ranges from 14 to 60, and their mixtures, and more particularly from the block copolymers of formula (I) having an HLB ranging from 2 to 16.

These block copolymers can be selected, in particular, from poloxamers and in particular from Poloxamer 231, such as the product sold by ICI under the name Pluronic L81, of formula (I) where x=z=6 and y=39 (HLB 2); Poloxamer 282, such as the product sold by ICI under the name Pluronic L92, of formula (I) where x=z=10 and y=47 (HLB 6); and Poloxamer 124, such as the product sold by ICI under the name Pluronic L44, of formula (I) where x=z=11 and y=21 (HLB 16).

The amount of surfactant in the nanoemulsion of the invention can range, for example, from 0.2 to 15% by weight, preferably from 1 to 8% by weight with respect to the total weight of the nanoemulsion.

The ratio by weight of the amount of the oily phase to the amount of surfactant ranges from 2 to 10, preferably from 3 to 6. The term «amount of oily phase» is understood here to mean the total amount of the constituents of this phase without including the amount of surfactant.

The nanoemulsion of the invention comprises at least one oil with a molecular weight of greater than 400. Oils with a molecular weight of greater than 400 can be selected from oils of animal or vegetable origin, mineral oils, synthetic oils and silicone oils, and their mixtures. Suitable oils of this type, of, for example, include isocetyl palmitate, isocetyl stearate, avocado oil and jojoba oil.

In addition, the oily phase can optionally comprise other oils and, in particular, oils having a molecular weight of less than 400. These oils are also selected from oils of animal and vegetable origin, mineral oils, synthetic oils and silicone oils. Suitable oils with a molecular weight of less than 400 include isododecane, isohexadecane, volatile silicone oils, isopropyl myristate, isopropyl palmitate and $C_{11}$–$C_{13}$ isoparaffin.

The oily phase can also comprise fatty substances other than the oils indicated above, such as fatty alcohols, for example stearyl, cetyl and behenyl alcohols, fatty acids, for example stearic, palmitic and behenic acids, oils of the fluorinated type, waxes, gums and their mixtures.

The nanoemulsions of the invention comprise an amount of oily phase preferably ranging from 2 to 40% and better still from 5 to 30% by weight with respect to the total weight of the nanoemulsion, the proportion of oil(s) having a molecular weight of greater than 400 preferably representing at least 40% by weight of the oily phase.

According to a specific embodiment of the invention, the nanoemulsion of the invention additionally comprises one or more ionic amphiphilic lipids.

The ionic amphiphilic lipids which can be used in the nanoemulsions of the invention are preferably selected from the group of anionic amphiphilic lipids, cationic amphiphilic lipids and alkylsulphonic derivatives.

The anionic amphiphilic lipids can be more particularly selected from the group of:

- the alkaline salts of dicetyl and dimyristyl phosphate;
- the alkaline salts of cholesterol sulfate;
- the alkaline salts of cholesterol phosphate;
- lipoamino acids and their salts, such as mono- and disodium acylglutamates, such as the disodium salt of N-stearoyl-L-glutamic acid sold under the name Acylglutamate HS21 by Ajinomoto;
- the sodium salts of phosphatidic acid;
- phospholipids.

The alkylsulfonic derivatives can more particularly be selected from the group of alkylsulfonic derivatives of formula (I):

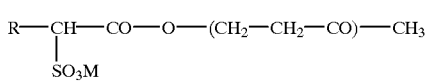

(I)

wherein R represents an alkyl radical comprising from 16 to 22 carbon atoms, in particular the $C_{16}H_{33}$ and $C_{18}H_{37}$ radicals, taken as a mixture or separately, and M is an alkali metal, such as sodium.

The cationic amphiphilic lipids can more particularly be selected from the group of quaternary ammonium salts, fatty amines and their salts.

The quaternary ammonium salts include, for example:

those which exhibit the following formula (II):

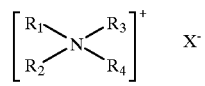

(II)

wherein the $R_1$ to $R_4$ radicals, which can be identical or different, represent a linear or branched aliphatic radical comprising from 1 to 30 carbon atoms or an aromatic radical, such as aryl or alkylaryl. The aliphatic radicals can comprise heteroatoms, such as, in particular, oxygen, nitrogen, sulfur and halogens. The aliphatic radicals include, for example, alkyl, alkoxy, polyoxy($C_2$–$C_6$)alkylene, alkylamido, ($C_{12}$–$C_{22}$)alkylamido($C_2$–$C_6$)alkyl, ($C_{12}$–$C_{22}$) alkyl acetate and hydroxyalkyl radicals comprising approximately from 1 to 30 carbon atoms; X is an anion selected from the group of the halides, phosphates, acetates, lactates, ($C_2$–$C_6$)alkyl sulfates, and alkyl- or alkylarylsulfonates. Preference is given, as quaternary ammonium salts of formula (II), to, on the one hand, tetraalkylammonium chlorides, such as, for example, dialkyldimethylammonium and alkyltrimethylammonium chlorides in which the alkyl radical comprises approximately from 12 to 22 carbon atoms, in particular behenyltrimethylammonium, distearyldimethylammonium, cetyltrimethylammonium and benzyldimethylstearylammonium chlorides, or alternatively, stearamidopropyldimethyl(myristyl acetate)ammonium chloride, sold under the name «CERAPHYL 70» by Van Dyk.

imidazolinium quaternary ammonium salts, such as, for example, those of formula (III):

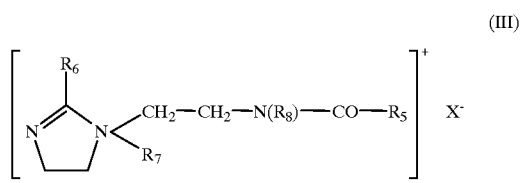

(III)

wherein $R_5$ represents an alkenyl or alkyl radical comprising from 8 to 30 carbon atoms, for example derived from tallow fatty acids; $R_6$ represents a hydrogen atom, an alkyl radical comprising from 1 to 4 carbon atoms or an alkenyl or alkyl radical comprising from 8 to 30 carbon atoms; $R_7$ represents an alkyl radical comprising from 1 to 4 carbon atoms; $R_8$ represents a hydrogen atom or an alkyl radical comprising from 1 to 4 carbon atoms; and X is an anion selected from the group of the halides, phosphates, acetates, lactates, alkyl sulfates, or alkyl- and alkylarylsulfonates. $R_5$ and $R_6$ preferably denote a mixture of alkenyl or alkyl radicals comprising from 12 to 21 carbon atoms, for example derived from tallow fatty acids, $R_7$ preferably denotes a methyl radical and $R_8$ preferably denotes hydrogen. Such a product is, for example, sold under the name «REWOQUAT W 75» by Rewo.

quaternary diammonium salts of formula (IV):

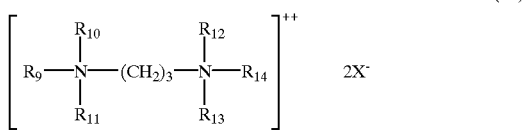

wherein $R_9$ denotes an aliphatic radical comprising approximately from 16 to 30 carbon atoms; $R_{10}$, $R_{11}$, $R_{12}$, $R_{13}$ and $R_{14}$ are selected from hydrogen and an alkyl radical comprising from 1 to 4 carbon atoms; and X is an anion selected from the group of the halides, acetates, phosphates, nitrates and methyl sulfates.

Such quaternary diammonium salts comprise in particular propanetallowdiammonium dichloride.

According to a preferred embodiment of the invention, a lipoamino acid is used as ionic amphiphilic lipid.

The ionic amphiphilic lipids can be introduced into one or the other phase of the nanoemulsion. When they are present in the nanoemulsion of the invention, they can be used in concentrations preferably ranging from 0.01 to 5% by weight and more particularly from 0.25 to 1% by weight with respect to the total weight of the nanoemulsion.

The emulsions in accordance with the present invention can comprise additives for improving the transparency of the formulation.

These additives are preferably selected from the group of:
   lower alcohols comprising from 1 to 8 carbon atoms and more particularly from 2 to 6 carbon atoms, such as ethanol;
   glycols, such as glycerol, propylene glycol, 1,3-butylene glycol, dipropylene glycol, pentylene glycol, isoprene glycol and polyethylene glycols comprising from 4 to 16, preferably from 8 to 12 ethylene oxide units;
   sugars, such as glucose, fructose, maltose, lactose or sucrose.

These additives can be used as a mixture. When they are present in the nanoemulsion of the invention, they can be used at concentrations preferably ranging from 0.01 to 3% by weight with respect to the total weight of the nanoemulsion and better still from 5 to 20% by weight with respect to the total weight of the nanoemulsion. The amount of alcohol (s) and/or of sugar(s) preferably ranges from 5 to 20% by weight with respect to the total weight of the nanoemulsion and the amount of glycol(s) preferably ranges from 5 to 15% by weight with respect to the total weight of the nanoemulsion.

In addition, the use of the alcohols as defined above at concentrations greater than or equal to 15% by weight makes it possible to obtain preservative-free emulsions.

The nanoemulsions defined above can be used in any field where this type of composition is useful. They can constitute in particular compositions for topical use and in particular cosmetic or dermatological compositions. They can also be used as ophthalmic vehicles. In addition, they can constitute, in the pharmaceutical field, a pharmaceutical composition which can be administered orally, parenterally or transcutaneously.

Another aspect of the invention is, therefore, a composition for topical use, which comprises a nanoemulsion as defined above.

A composition for topical or pharmaceutical use comprises a physiologically acceptable medium, that is to say compatible with the skin, mucous membranes, scalp, eyes and/or hair.

Another aspect of the invention is an ophthalmic vehicle, which comprises a nanoemulsion as defined above.

Still another aspect of the invention is a pharmaceutical composition, which comprises a nanoemulsion as defined above.

The nanoemulsions of the invention can comprise water-soluble or fat-soluble active principles having a cosmetic, dermatological or ophthalmic activity. The fat-soluble active principles are in the oily globules of the emulsion, whereas the water-soluble active principles are in the aqueous phase of the emulsion. Suitable examples of active principles include vitamins, such as vitamin E, and their derivatives and in particular their esters, provitamins, such as panthenol, humectants and sun-screen agents.

Suitable ophthalmic active principles include, for example, antiglaucoma agents, such as betaxolol; antibiotics, such as acyclovir; antiallergics; anti-inflammatory agents, such as ibuprofen and its salts, diclofenac and its salts, or indomethacin; or antiviral agents.

The nanoemulsions of the invention can be provided in the form of a lotion, serum, cream, milk or toilet water and can comprise adjuvants commonly used in the cosmetics, dermatological and ophthalmic fields, such as, for example, gelling agents, preservatives, antioxidants and fragrances. They can also be provided in the form of an eye lotion, in particular for ophthalmological applications.

Suitable gelling agents which can be used, include cellulose derivatives, algal derivatives, natural gums and synthetic polymers, such as polymers and copolymers of carboxyvinyl acids, for example, those sold under the name Carbopol by Goodrich.

Another aspect of the invention is a process for the preparation of a nanoemulsion as defined above, this process comprising the mixing of the aqueous phase and the oily phase with vigorous stirring at a temperature ranging from 10 to 80° C. and then a homogenization of the mixture at a pressure preferably ranging from $6 \times 10^7$ Pa to $18 \times 10^7$ Pa (high-pressure homogenization). The shearing preferably ranges from $2 \times 10^6$ $s^{-1}$ to $5 \times 10^8$ $s^{-1}$, better still from $1 \times 10^8$ $s^{-1}$ to $3 \times 10^8$ $s^{-1}$ ($s^{-1}$ signifies second$^{-1}$).

The nanoemulsion of the invention can be used, for example, for caring, for treating or making-up the skin, face and/or scalp.

Yet another aspect of the invention is the cosmetic use of the nanoemulsion as defined above for caring for, treating and/or making-up the skin, face and/or scalp.

In addition, the nanoemulsion of the invention can also be used for caring for and/or treating the hair. The invention makes it possible to obtain a deposit of oil on the hair, which renders the latter glossier and more resistant to styling, without, however, making it lank. It also makes it possible, as a pretreatment, to improve the effects of dyeing or permanent waving of the hair.

Another aspect of the invention is the cosmetic use of the nanoemulsion as defined above for caring for and/or treating the hair.

The nanoemulsion of the invention makes possible, in particular, good moisturizing of the skin, mucous membranes and/or scalp and is particularly suited to the treatment of dry skin.

Another aspect of the invention is, therefore, a cosmetic process for caring for and/or moisturizing the skin, mucous membranes and/or scalp, wherein the nanoemulsion as defined above is applied to the skin, mucous membranes and/or scalp.

The invention also relates to the use of the nanoemulsion of the invention in the manufacture of a dermatological composition intended for the treatment of dry skin.

Finally, the invention also relates to the use of the nanoemulsion of the invention in the manufacture of an ophthalmological composition.

Having now generally described this invention, a further understanding can be obtained by reference to certain specific examples which are provided herein for purposes of illustration only and are not intended to be limiting unless otherwise specified. The amounts shown below are in % by weight.

EXAMPLES

Example 1: Fluid make-up remover

| Oily phase: | |
|---|---|
| Disodium salt of N-stearoyl-L-glutamic acid (Acylglutamate HS21 from Ajinomoto) | 0.5% |
| Poloxamer 124 (Pluronic L44 from ICI) | 4.5% |
| Isocetyl stearate (M.W. = 508) | 10% |
| Isododecane (M.W. = 170) | 5% |
| Aqueous phase: | |
| Glycerol | 5% |
| Dipropylene glycol | 10% |
| Water | 65% |

A transparent nanoemulsion is obtained, the size of the globules of which is 46 nm and the turbidity of which is 130 NTU.

Example 2: Make-up removing gel

| Oily phase: | |
|---|---|
| Poloxamer 231 (Pluronic L81 from ICI) | 4.5% |
| Disodium salt of N-stearoyl-L-glutamic acid (Acylglutamate HS21 from Ajinomoto) | 0.5% |
| Isocetyl stearate (M.W. = 508) | 16% |
| Isopropyl myristate (M.W. = 270) | 4% |
| Aqueous phase: | |
| Glycerol | 5% |
| Dipropylene glycol | 10% |
| Water | 60% |

A gelled transparent nanoemulsion is obtained, the size of the globules of which is 54 nm and the turbidity of which is 256 NTU.

Example 3: Eye lotion

| Oily phase: | |
|---|---|
| Poloxamer 282 (Pluronic L92 from ICI) | 0.75% |
| Disodium salt of N-stearoyl-L-glutamic acid (Acylglutamate HS21 from Ajinomoto) | 0.08% |
| Soybean oil (M.W. of the order of 900) | 1.67% |
| Isopropyl myristate (M.W. = 270) | 0.83% |
| Aqueous phase: | |
| Glycerol | 0.83% |
| Dipropylene glycol | 1.67% |
| Water q.s. for | 100% |

A transparent nanoemulsion is obtained, the size of the globules of which is 44 nm and the turbidity of which is 110 NTU.

The disclosure of French priority Application Number 9900031 filed Jan. 1, 1999 is hereby incorporated by reference into the present application.

Obviously, numerous modifications and variations of the present invention are possible in light of the above teachings. It is, therefore, to be understood that within the scope of the appended claims, the invention may be practised otherwise than as specifically described herein

What is claimed as new and is intended to be secured by Letters Patent is:

1. A nanoemulsion, comprising: an oily phase dispersed in an aqueous phase in the form of oil globules having a number-average size of less than 100 nm and at least one additive selected from the group consisting of alcohols, glycols and mixtures thereof, which dispersion is facilitated by a surfactant comprised of polyethylene oxide and polypropylene oxide blocks, the oily phase comprising at least one cosmetically, dermatologically and ophthalmologically acceptable oil having a molecular weight of greater than 400 and wherein the ratio by weight of the amount of oily phase to the amount of surfactant ranges from 2 to 10, the nanoemulsion being useful in cosmetic and dermatological applications.

2. The nanoemulsion according to claim 1, which has a turbidity ranging from 60 to 600 NTU.

3. The nanoemulsion according to claim 1, wherein the amount of surfactant ranges from 0.2 to 15% by weight with respect to the total weight of the nanoemulsion.

4. The nanoemulsion according to claim 1, wherein the amount of surfactant ranges from 1 to 8% by weight with respect to the total weight of the nanoemulsion.

5. The nanoemulsion according to claim 1, wherein the ratio by weight of the amount of oily phase to the amount of surfactant ranges from 3 to 6.

6. The nanoemulsion according to claim 1, wherein the oil globules have an average size ranging from 20 to 75 nm.

7. The nanoemulsion according to claim 1, wherein the surfactant is selected from the group consisting of three polyoxyethylene, polyoxypropylene block copolymers having formula (1): $HO(C_2H_4O)_x(C_3H_6O)_y(C_2H_4O)_zH$, wherein the average values of x, y and z of one copolymer are 6, 39 and 6; the average values of x, y and z of a second copolymer are 10, 47 and 10; and the average values of x, y and z are 11, 21 and 11 for a third copolymer and their mixtures.

8. The nanoemulsion according to claim 1, wherein the oil with a molecular weight of greater than 400 is selected from the group consisting of oils of animal or vegetable origin, mineral oils, synthetic oils and silicone oils, and their mixtures.

9. The nanoemulsion according to claim 1, wherein the oily phase additionally comprises at least one oil having a molecular weight of less than 400.

10. The nanoemulsion according to claim 1, wherein the oily phase comprises at least 40% by weight of oil(s) having a molecular weight of greater than 400 with respect to the total weight of the oily phase.

11. The nanoemulsion according to claim 1, wherein the amount of oily phase ranges from 2 to 40% by weight with respect to the total weight of the nanoemulsion.

12. The nanoemulsion according to claim 1, wherein the nanoemulsion additionally comprises at least one ionic amphiphilic lipid selected from the group consisting of anionic amphiphilic lipids, cationic amphiphilic lipids and alkylsulfonic derivatives.

13. The nanoemulsion according to claim 12, wherein the ionic amphiphilic lipids are selected from the group consisting of:

the alkaline salts of dicetyl and dimyristyl phosphate;

the alkaline salts of cholesterol sulfate;

the alkaline salts of cholesterol phosphate;

the salts of lipoamino acids;

the sodium salts of phosphatidic acid;

phospholipids;

the alkylsulfonic derivatives of formula (I):

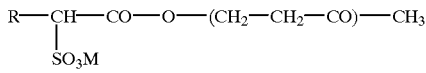

(I)

wherein R represents $C_{16}$–$C_{22}$ alkyl radicals, taken as a mixture or separately, and M is an alkali metal, a quaternary ammonium ion, a fatty amine or a salt thereof, and their mixtures.

14. The nanoemulsion according to claim 12, wherein the amount of ionic amphiphilic lipid(s) ranges from 0.01 to 5% by weight with respect to the total weight of the nanoemulsion.

15. The nanoemulsion according to claim 1, wherein the additive is present in a concentration ranging from 5 to 20% by weight with respect to the total weight of the nanoemulsion.

16. The nanoemulsion according to claim 1, which further comprises a cosmetic, dermatological or ophthalmological active principle.

17. A composition for topical application which comprises the nanoemulsion according to claim 1.

18. An ophthalmic vehicle, which comprises the nanoemulsion according to claim 1.

19. A pharmaceutical composition, which comprises the nanoemulsion according to claim 1.

20. A method of cosmetically treating skin, comprising:
applying the nanoemulsion according to claim 1 to the skin in order to care for, treat and/or make-up the skin of the body, face and/or scalp.

21. A method of cosmetically treating hair, comprising:
applying the nanoemulsion according to claim 1 to the hair in order to care for and/or treat the hair.

22. A method of cosmetic treatment, comprising:
applying the nanoemulsion according to claim 1 to the skin, mucous membranes and/or scalp for the care of and/or the moisturizing of the skin, mucous membranes and/or scalp.

23. A method of manufacturing a dermatological composition, comprising:
formulating the composition with the nanoemulsion according to claim 1 for the treatment of dry skin.

24. A method of manufacturing a ophthalmological composition, comprising:
formulating the composition with the nanoemulsion according to claim 1.

25. A process for the preparation of the nanoemulsion of claim 1, which comprises:
mixing said aqueous phase and said oily phase with vigorous stirring at an ambient temperature ranging from 10 to 80° C., and then
homogenizing the mixture at a pressure ranging from $6 \times 10^7$ Pa to $18 \times 10^7$ Pa.

26. The process according to claim 27, wherein the shearing ranges from $2 \times 10^6$ s$^{-1}$ to $5 \times 10^8$ s$^{-1}$.

* * * * *

UNITED STATES PATENT AND TRADEMARK OFFICE
CERTIFICATE OF CORRECTION

PATENT NO. : 6,464,990 B2
DATED : October 15, 2002
INVENTOR(S) : Jean-Thierry Simonnet et al.

It is certified that error appears in the above-identified patent and that said Letters Patent is hereby corrected as shown below:

Column 10,
Line 30, "claim 27" should read -- claim 25 --.

Please add new Claim 27 as follows:

-- 27. (Newly Added) The nanoemulsion according to Claim 1, wherein the surfactant is a block copolymer of formula (I) having an HLB ranging from 2 to 16:

$$HO(C_2H_4O)_x(C_3H_6O)_y(C_2H_4O)_zH,$$

wherein x, y and z are integers such that x+z ranges from 2 to 100 and y ranges from 14 to 60, and mixtures of individual surfactants within the scope of the formula. --

Signed and Sealed this

Seventeenth Day of June, 2003

JAMES E. ROGAN
*Director of the United States Patent and Trademark Office*